US008663733B2

(12) United States Patent
Barthel et al.

(10) Patent No.: US 8,663,733 B2
(45) Date of Patent: *Mar. 4, 2014

(54) METHOD FOR COATING WATER-ABSORBING POLYMER PARTICLES

(75) Inventors: Holger Barthel, Oftersheim (DE); Martin Wendker, Wentorf (DE); Reiner Witt, St. Leon-Rot (DE); Karin Flore, Worms (DE)

(73) Assignee: BASF SE, Ludwigshafen (DE)

( * ) Notice: Subject to any disclaimer, the term of this patent is extended or adjusted under 35 U.S.C. 154(b) by 470 days.

This patent is subject to a terminal disclaimer.

(21) Appl. No.: 12/528,951

(22) PCT Filed: Mar. 17, 2008

(86) PCT No.: PCT/EP2008/053171
§ 371 (c)(1),
(2), (4) Date: Aug. 27, 2009

(87) PCT Pub. No.: WO2008/113789
PCT Pub. Date: Sep. 25, 2008

(65) Prior Publication Data
US 2010/0047445 A1   Feb. 25, 2010

(30) Foreign Application Priority Data
Mar. 19, 2007 (EP) ..................... 07104409

(51) Int. Cl.
*B05D 7/00* (2006.01)
(52) U.S. Cl.
USPC ............ 427/212; 427/222; 427/422; 428/403
(58) Field of Classification Search
USPC ............ 427/212, 213, 213.3, 213.31–213.36, 427/214, 220, 221, 222, 372.2, 421.1, 422, 427/427.4; 118/302, 303; 264/4.1, 4.3; 428/403, 407
See application file for complete search history.

(56) References Cited

U.S. PATENT DOCUMENTS

| 4,217,851 | A | * | 8/1980 | Biehl et al. ...................... 118/20 |
| 4,666,983 | A | | 5/1987 | Tsubakimoto et al. |
| 4,749,595 | A | * | 6/1988 | Honda et al. .................. 427/213 |
| 6,866,935 | B1 | * | 3/2005 | Lee et al. ...................... 428/403 |
| 2004/0181031 | A1 | | 9/2004 | Nogi et al. |
| 2004/0186244 | A1 | | 9/2004 | Hatsuda et al. |
| 2004/0240316 | A1 | * | 12/2004 | Nogi et al. .................. 366/348 |
| 2007/0264435 | A1 | * | 11/2007 | Venett et al. ................. 427/422 |

FOREIGN PATENT DOCUMENTS

| DE | 33 14 019 A1 | 1/1984 |
| DE | 197 18 664 A1 | 11/1998 |
| EP | 1 191 051 A2 | 3/2002 |
| WO | WO 00/78953 | 12/2000 |
| WO | WO-2006/082242 A2 | 8/2006 |

OTHER PUBLICATIONS

"Different Methods of Batch and Continuous Mixing of Solids" Gericke Feb. 1993.*
Buchholz et al. (eds.), *Modern Superabsorbent Polymer Technology*, pp. 71-103, New York: Wiley-VCH (1998).
International Preliminary Report on Patentability (English Translation) for corresponding International Application No. PCT/EP2008/053171, dated Oct. 15, 2009.
International Search Report for corresponding International Application No. PCT/EP2008/053171, dated Jul. 23, 2008.
Data sheet of the firm H. Ikeuchi & Co. Ltd., 3-Piece Structure Standard Flat Spray Nozzles, undated, pp. 12-14.
BASF, Technical Bulletin, "Lupamin® 9095 High Molecular Weight Linear Polyvinylamine" (2002).
Vauck, W., et al. *Grundoperationen Chemischer Verfahrenstechnik*, Wiley-VCH Verlag GmbH & Co. KGaA (11th ed., revised and enlarged), Oct. 28, 1999, pp. 371-375.
Hosokawa-Schugi, User's Manual, Schugi Flexomix, Kontinuierliche Misch- und Agglomeriermaschine 335 (2005), p. 2.

* cited by examiner

*Primary Examiner* — John Goff
(74) *Attorney, Agent, or Firm* — Marshall, Gerstein & Borun LLP

(57) ABSTRACT

A process for preparing water-absorbing polymer particles by spraying a liquid onto water-absorbing polymer particles by means of at least one thermally insulated and/or trace-heated spray nozzle in a mixer.

20 Claims, No Drawings

METHOD FOR COATING WATER-ABSORBING POLYMER PARTICLES

CROSS-REFERENCE TO RELATED APPLICATIONS

This is the U.S. national phase of International Application No. PCT/EP2008/053171, filed Mar. 17, 2008, which claims the benefit of European Patent Application No. 07104409.3, filed Mar. 19, 2007.

The present invention relates to a process for preparing water-absorbing polymer particles by spraying a liquid onto water-absorbing polymer particles by means of at least one thermally insulated and/or trace-heated spray nozzle in a mixer.

The preparation of water-absorbing polymer particles is described in the monograph "Modern Superabsorbent Polymer Technology", F. L. Buchholz and A. T. Graham, Wiley-VCH, 1998, pages 71 to 103.

Being products which absorb aqueous solutions, water-absorbing polymers are used to produce diapers, tampons, sanitary napkins and other hygiene articles, but also as a water-retaining agent in market gardening.

The properties of the water-absorbing polymers can be adjusted via the degree of crosslinking. With increasing degree of crosslinking, the gel strength rises and the centrifuge retention capacity (CRC) falls.

To improve the use properties, for example permeability of the swollen gel bed (SFC) in the diaper and absorbency under load (AUL0.9 psi), water-absorbing polymer particles are generally postcrosslinked. This increases only the degree of crosslinking of the particle surface, which allows absorbency under load (AUL0.9 psi) and centrifuge retention capacity (CRC) to be at least partly decoupled. This postcrosslinking can be performed in the aqueous gel phase. However, dried, ground and screened-off polymer particles (base polymer) are preferably coated with a postcrosslinker on the surface, thermally crosslinked and dried. Crosslinkers suitable for this purpose are compounds which comprise at least two groups which can form covalent bonds with the carboxylate groups of the water-absorbing polymers.

To further improve the permeability (SFC), the particle surface can be modified further, for example by coating with inorganic inert substances, cationic polymers and/or solutions of polyvalent metal cations.

EP 1 191 051 A2 describes spray nozzles with a wide spray angle for use in the postcrosslinking of water-absorbing polymer particles. The postcrosslinker solution to be sprayed on preferably has a lower temperature than the initially charged water-absorbing polymer particles.

US 2004/0181031 A1 discloses a process for postcrosslinking, wherein the water-absorbing polymer particles are cooled in an air stream after the thermal postcrosslinking.

It was an object of the present invention to provide an improved coating process for water-absorbing polymer particle.

It was a further object to find a coating process which enables the production of very uniformly coated water-absorbing polymer particles with high permeability (SFC) and low dust content.

It was a further object of the invention to provide a coating process which is not prone to disruption.

The object is achieved by a process for producing water-absorbing polymer particles by polymerizing a monomer solution or suspension comprising a) at least one ethylenically unsaturated acid-bearing monomer which may be at least partly neutralized, b) at least one crosslinker, c) optionally one or more ethylenically and/or allylically unsaturated monomers copolymerizable with the monomers specified under a) and d) optionally one or more water-soluble polymers, comprising drying, grinding and classifying, a liquid being sprayed onto the water-absorbing polymer particles by means of at least one spray nozzle in a mixer, wherein the at least one spray nozzle is thermally insulated and/or trace-heated.

"Thermally insulated" means that the outer surface of the spray nozzle at least partly has a further material layer, the material of the further material layer having a lower thermal conductivity than the material of the spray nozzle. The thermal conductivity of the material of the further material layer at 20° C. is preferably less than 2 $Wm^{-1}K^{-1}$, more preferably less than 0.5 $Wm^{-1}K^{-1}$, most preferably less than 0.1 $Wm^{-1}K^{-1}$.

"Trace-heated" means that thermal energy is additionally supplied to the spray nozzle, for example by means of electrical energy or by means of a heating jacket flowed through by a heat carrier. Suitable heat carriers are commercial heat carrier oils, such as Marlotherm®, steam or hot water.

Possible heat supply via one of the feed stocks used in the mixing, i.e. water-absorbing polymer particles or liquid to be sprayed, is not trace heating in the sense of the present invention.

Suitable liquids are, as well as pure substances which are liquid at 23° C., also solutions, dispersions, emulsions and melts. The process according to the invention is especially suitable for coating with aqueous solutions or dispersions.

The process according to the invention preferably comprises at least one postcrosslinking. In a particularly preferred embodiment of the present invention, the liquid is sprayed onto postcrosslinked polymer particles.

The process according to the invention is not prone to disruption and is therefore particularly suitable for continuous mixers.

The fill level of the mixer is preferably from 30 to 80%, more preferably from 40 to 75%, most preferably from 50 to 70%.

Too high a water content increases the agglomeration tendency of the water-absorbing polymer particles. The water content of the water-absorbing polymer particles to be used in the process according to the invention is therefore preferably less than 20% by weight, more preferably less than 10% by weight, most preferably less than 1% by weight.

The temperature of the water-absorbing polymer particles is preferably from 40 to 80° C., more preferably from 45 to 75° C., most preferably from 50 to 70° C.

The temperature of the spray nozzle is preferably from 1 to 20° C., more preferably from 2 to 15° C., most preferably from 5 to 10° C., higher than the temperature of the water-absorbing polymer particles.

In the case of a thermally insulated spray nozzle, the temperature of the liquid to be sprayed is preferably from 1 to 20° C., more preferably from 2 to 15° C., most preferably from 5 to 10° C., higher than the temperature of the water-absorbing polymer particles. The temperature of the liquid to be sprayed corresponds roughly to the temperature of the spray nozzle.

In the case of a trace-heated and optionally thermally insulated spray nozzle, the temperature difference between the water-absorbing polymer particles and the liquid to be sprayed on is preferably less than 20° C., preferentially less than 10° C., more preferably less than 5° C., most preferably less than 2° C.

The liquid is preferably sprayed on by means of a two-substance nozzle, more preferably by means of an internally mixing two-substance nozzle.

Two-substance nozzles enable atomization into fine droplets or a spray mist. The atomization form employed is a circular or else elliptical solid or hollow cone. Two-substance nozzles may be configured with external mixing or internal mixing. In the externally mixing two-substance nozzles, liquid and atomizer gas leave the nozzle head through separate orifices. They are mixed in the spray jet only after they leave the spray nozzle. This enables independent regulation of droplet size distribution and throughput within a wide range. The spray cone of the spray nozzle can be adjusted via the air cap setting. In the internally mixing two-substance nozzle, liquid and atomizer gas are mixed within the spray nozzle and the biphasic mixture leaves the nozzle head through the same bore (or through a plurality of bores connected in parallel). In the internally mixing two-substance nozzle, the quantitative ratios and pressure conditions are more highly coupled than in the externally mixing spray nozzle. Small changes in the throughput therefore lead to a change in the droplet size distribution. The adjustment to the desired throughput is effected through the selected cross section of the nozzle bore.

Useful atomizer gases include compressed air, gas or steam of 0.5 bar and more. The droplet size may be adjusted individually via the ratio of the liquid mass flow rate to atomizer gas mass flow rate, and also gas and liquid pressure.

The temperature difference between the liquid to be sprayed on and the atomizer gas is preferably less than 20° C., preferentially less than 10° C., more preferably less than 5° C., most preferably less than 2° C.

In the process according to the invention, it is possible to use all mixers known to those skilled in the art. The liquid can be sprayed on either in high-speed mixers or in mixers with low stirrer speed. Preference is given to using mixers with moving mixing tools, such as screw mixers, disk mixers, plowshare mixers, paddle mixers, screw belt mixers, Schugi mixers and continuous flow mixers.

Mixers with rotating mixing tools are divided into vertical mixers and horizontal mixers according to the position of the axis of rotation. A preferred vertical mixer is the Schugi mixer. A preferred horizontal mixer is the continuous flow mixer.

The residence time in the vertical mixer is preferably from 0.1 to 15 seconds, more preferably from 0.25 to 10 seconds, most preferably from 0.5 to 5 seconds.

The peripheral speed of the mixing tools in the vertical mixer is preferably from 2.5 to 50 m/s, more preferably from 5 to 40 m/s, most preferably from 10 to 30 m/s.

The residence time in the horizontal mixer is preferably from 1 to 180 minutes, more preferably from 2 to 60 minutes, most preferably from 5 to 20 minutes.

The peripheral speed of the mixing tools in the horizontal mixer is preferably from 0.1 to 10 m/s, more preferably from 0.5 to 5 m/s, most preferably from 0.75 to 2.5 m/s.

The water-absorbing polymer particles are moved in the horizontal mixer with a speed which corresponds to a Froude number of preferably from 0.01 to 6, more preferably from 0.05 to 3, most preferably from 0.1 to 0.7.

For mixers with horizontally mounted mixing tools, the Froude number is defined as follows:

$$Fr = \frac{\omega^2 r}{g}$$

where
r: radius of the mixing tool
ω: circular frequency
g: acceleration due to gravity In a particularly preferred embodiment, the liquid is sprayed below the product bed surface of the moving polymer particle layer, preferably at least 10 mm, more preferably at least 50 mm, most preferably at least 100 mm, i.e. the spray nozzle is immersed into the product bed.

The product bed surface is the interface which is established between the water-absorbing polymer particles moved within the mixer and the atmosphere above.

In the horizontal mixer, the angle between the mixer axis and the supply to the spray nozzle is preferably approx. 90°. The liquid can be supplied vertically from the top. Supply at an oblique angle from the side is likewise possible, in which case the angle relative to the vertical is preferably between 60 and 90°, more preferably between 70 and 85°, most preferably between 75 and 82.5°. The oblique arrangement of the supply enables the use of shorter supply lines and hence lower mechanical stresses during the operation of the mixer.

In a particularly preferred embodiment, the spray nozzle is disposed below the axis of rotation and sprays in the direction of rotation. As a result of this arrangement, the coated water-absorbing polymer particles are conveyed away from the spray nozzle in an optimal manner. In combination with the oblique arrangement, it is also possible to exchange the spray nozzle during the operation of the mixer without the product being discharged.

Suitable liquids are, for example, dispersions of inorganic inert substances, solutions or dispersions of cationic polymers, solutions of di- or polyvalent metal cations, and also polyols or solutions thereof.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 50 g/100 g of water, and preferably have at least one acid group each.

Suitable monomers a) are, for example, ethylenically unsaturated carboxylic acids such as acrylic acid, methacrylic acid, maleic acid, fumaric acid and itaconic acid. Particularly preferred monomers are acrylic acid and methacrylic acid. Very particular preference is given to acrylic acid.

The proportion of acrylic acid and/or salts thereof in the total amount of monomers a) is preferably at least 50 mol %, more preferably at least 90 mol %, most preferably at least 95 mol %.

The monomers a), especially acrylic acid, comprise preferably up to 0.025% by weight of a hydroquinone monoether. Preferred hydroquinone monoethers are hydroquinone monomethyl ether (MEHQ) and/or tocopherols.

Tocopherol is understood to mean compounds of the following formula

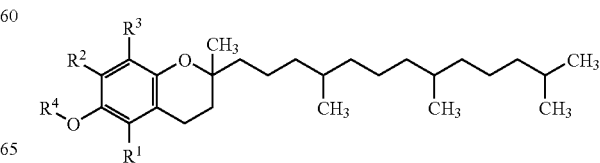

where $R^1$ is hydrogen or methyl, $R^2$ is hydrogen or methyl, $R^3$ is hydrogen or methyl, and $R^4$ is hydrogen or an acyl radical having from 1 to 20 carbon atoms.

Preferred radicals for $R^4$ are acetyl, ascorbyl, succinyl, nicotinyl and other physiologically compatible carboxylic acids. The carboxylic acids may be mono-, di- or tricarboxylic acids.

Preference is given to alpha-tocopherol where $R^1=R^2=R^3=$methyl, in particular racemic alpha-tocopherol. $R^1$ is more preferably hydrogen or acetyl. RRR-alpha-tocopherol is especially preferred.

The monomer solution comprises preferably at most 130 ppm by weight, more preferably at most 70 ppm by weight, preferably at least 10 ppm by weight, more preferably at least 30 ppm by weight, in particular around 50 ppm by weight, of hydroquinone monoether, based in each case on acrylic acid, acrylic acid salts also being considered as acrylic acid. For example, the monomer solution can be prepared by using acrylic acid having an appropriate content of hydroquinone monoether.

Crosslinkers b) are compounds having at least two polymerizable groups which can be polymerized by a free-radical mechanism into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate or ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and vinylphosphonic acid derivatives, as described, for example, in EP 343 427 A2. Further suitable crosslinkers b) are pentaerythritol diallyl ether, pentaerythritol triallyl ether and pentaerythritol tetraallyl ether, polyethylene glycol diallyl ether, ethylene glycol diallyl ether, glycerol diallyl ether and glycerol triallyl ether, polyallyl ethers based on sorbitol, and ethoxylated variants thereof. In the process according to the invention, it is possible to use di(meth)acrylates of polyethylene glycols, the polyethylene glycol used having a molecular weight between 100 and 1000.

However, particularly advantageous crosslinkers b) are di- and triacrylates of 3- to 20-tuply ethoxylated glycerol, of 3- to 20-tuply ethoxylated trimethylolpropane, of 3- to 20-tuply ethoxylated trimethylolethane, in particular di- and triacrylates of 2- to 6-tuply ethoxylated glycerol or of 2- to 6-tuply ethoxylated trimethylolpropane, of 3-tuply propoxylated glycerol or of 3-tuply propoxylated trimethylolpropane, and also of 3-tuply mixed ethoxylated or propoxylated glycerol or of 3-tuply mixed ethoxylated or propoxylated trimethylolpropane, of 15-tuply ethoxylated glycerol or of 15-tuply ethoxylated trimethylolpropane, and also of at least 40-tuply ethoxylated glycerol, of at least 40-tuply ethoxylated trimethylolethane or of at least 40-tuply ethoxylated trimethylolpropane.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 1 0-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol.

The amount of crosslinker b) is preferably from 0.01 to 15% by weight, more preferably from 0.5 to 10% by weight, most preferably from 1 to 5% by weight, based in each case on the monomer solution.

Examples of ethylenically unsaturated monomers c) which are copolymerizable with the ethylenically unsaturated, acid-bearing monomers a) are acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers d) include polyvinyl alcohol, polyvinylpyrrolidone, starch, starch derivatives, polyglycols or polyacrylic acids, preferably polyvinyl alcohol and starch.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. The oxygen content of the monomer solution is preferably lowered before the polymerization to less than 1 ppm by weight, more preferably to less than 0.5 ppm by weight.

The preparation of a suitable polymer and also further suitable hydrophilic ethylenically unsaturated monomers a) are described in DE 199 41 423 A1, EP 686 650 A1, WO 2001/45758 A1 and WO 2003/104300 A1.

Suitable reactors are kneading reactors or belt reactors. In the kneader, the polymer gel formed in the polymerization of an aqueous monomer solution is comminuted continuously by, for example, contrarotatory stirrer shafts, as described in WO 2001/38402 A1. The polymerization on the belt is described, for example, in DE 38 25 366 A1 and U.S. Pat. No. 6,241,928. Polymerization in a belt reactor forms a polymer gel which has to be comminuted in a further process step, for example in a meat grinder, extruder or kneader.

Advantageously, the hydrogel, after leaving the polymerization reactor, is then stored, for example in insulated vessels, at elevated temperature, preferably at least 50° C., more preferably at least 70° C., most preferably at least 80° C., and preferably less than 100° C. The storage, typically for from 2 to 12 hours, further increases the monomer conversion.

In the case of relatively high monomer conversions in the polymerization reactor, the storage can also be shortened significantly or a storage can be dispensed with.

The acid groups of the resulting hydrogels have typically been partially neutralized, preferably to an extent of from 25 to 95 mol %, more preferably to an extent of from 50 to 80 mol % and even more preferably to an extent of from 60 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

Neutralization is preferably carried out at the monomer stage. It is done typically by mixing in the neutralizing agent as an aqueous solution, as a melt, or else preferably as a solid material. For example, sodium hydroxide having a water content of distinctly below 50% by weight can be present as a waxy mass having a melting point of above 23° C. In this case, metering as piece material or melt at elevated temperature is possible.

However, it is also possible to carry out neutralization after the polymerization, at the hydrogel stage. It is also possible to neutralize up to 40 mol %, preferably from 10 to 30 mol % and more preferably from 15 to 25 mol % of the acid groups before the polymerization by adding a portion of the neutralizing agent actually to the monomer solution and setting the desired final degree of neutralization only after the polymerization, at the hydrogel stage. When the hydrogel is neutralized at least partly after the polymerization, the hydrogel is preferably comminuted mechanically, for example by means of a meat grinder, in which case the neutralizing agent can be sprayed, sprinkled or poured on and then carefully mixed in. To this end, the gel mass obtained can be repeatedly ground in a meat grinder for homogenization.

The hydrogel is then preferably dried with a belt dryer until the residual moisture content is preferably below 15% by weight and especially below 10% by weight, the water content being determined by EDANA (European Disposables and Nonwovens Association) recommended test method No. WSP 230.2-05 "Moisture content". If desired, however, drying can also be carried out using a fluidized bed dryer or a heated plowshare mixer. To obtain particularly white products, it is advantageous to dry this gel while ensuring rapid removal of the evaporating water. To this end, the dryer temperature must be optimized, the air feed and removal has to be controlled, and sufficient venting must be ensured in each case. The higher the solids content of the gel, the simpler the drying, by its nature, and the whiter the product. The solids content of the gel before the drying is therefore preferably between 30% and 80% by weight. It is particularly advantageous to vent the dryer with nitrogen or another nonoxidizing inert gas. If desired, however, it is also possible simply just to lower the partial pressure of the oxygen during the drying in order to prevent oxidative yellowing processes.

Thereafter, the dried hydrogel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of the EDANA (European Disposables and Nonwovens Association) recommended test method No. WSP 220.2-05 "Particle size distribution", where the proportions by mass of the screen fractions are plotted in cumulated form and the mean particle size is determined graphically. The mean particle size here is the value of the mesh size which gives rise to a cumulative 50% by weight.

To further improve the properties, the polymer particles may be postcrosslinked. Suitable postcrosslinkers are compounds which comprise at least two groups which can form covalent bonds with the carboxylate groups of the hydrogel. Suitable compounds are, for example, alkoxysilyl compounds, polyaziridines, polyamines, polyamidoamines, di- or polyepoxides, as described in EP 83 022 A2, EP 543 303 A1 and EP 937 736 A2, di- or polyfunctional alcohols, as described in DE 33 14 019 A1, DE 35 23 617 A1 and EP 450 922 A2, or β-hydroxyalkylamides, as described in DE 102 04 938 A1 and U.S. Pat. No. 6,239,230.

Additionally described as suitable postcrosslinkers are cyclic carbonates in DE 40 20 780 C1, 2-oxazolidone and its derivatives, such as 2-hydroxyethyl-2-oxazolidone, in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/31482 A1.

In addition, it is also possible to use postcrosslinkers which comprise additional polymerizable ethylenically unsaturated groups, as described in DE 37 13 601 A1.

The amount of postcrosslinker is preferably from 0.01 to 1% by weight, more preferably from 0.05 to 0.5% by weight, most preferably from 0.1 to 0.2% by weight, based in each case on the polymer.

In a preferred embodiment of the present invention, polyvalent cations are applied to the particle surface in addition to the postcrosslinkers.

The polyvalent cations usable in the process according to the invention are, for example, divalent cations such as the cations of zinc, magnesium, calcium and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate is preferred. Apart from metal salts, it is also possible to use polyamines as polyvalent cations.

The amount of polyvalent cation used is, for example, from 0.001 to 0.5% by weight, preferably from 0.005 to 0.2% by weight, more preferably from 0.02 to 0.1% by weight, based in each case on the polymer.

The postcrosslinking is typically performed in such a way that a solution of the postcrosslinker is sprayed onto the hydrogel or the dry polymer particles. After the spraying, the polymer particles coated with the postcrosslinker are dried thermally, and the postcrosslinking reaction can take place either before or during the drying.

The spraying of a solution of the postcrosslinker is preferably performed in mixers with moving mixing tools, such as screw mixers, paddle mixers, disk mixers, plowshare mixers and shovel mixers. Particular preference is given to horizontal mixers such as plowshare mixers and shovel mixers, very particular preference to vertical mixers. Suitable mixers are, for example, Lödige mixers, Bepex mixers, Nauta mixers, Processall mixers and Schugi mixers.

The thermal drying is preferably carried out in contact dryers, more preferably paddle dryers, most preferably disk dryers. Suitable dryers are, for example, Bepex dryers and Nara dryers. Moreover, it is also possible to use fluidized bed dryers.

The drying can be effected in the mixer itself, by heating the jacket or blowing in warm air. Equally suitable is a downstream dryer, for example a staged dryer, a rotary tube oven or a heatable screw. It is particularly advantageous to mix and dry in a fluidized bed dryer.

Preferred drying temperatures are in the range from 100 to 250° C., preferably from 120 to 220° C. and more preferably from 130 to 210° C. The preferred residence time at this temperature in the reaction mixer or dryer is preferably at least 10 minutes, more preferably at least 20 minutes, most preferably at least 30 minutes.

Subsequently, the postcrosslinked polymer can be classified again.

To further improve the properties, the postcrosslinked polymer particles can be coated. Suitable coatings for improving the acquisition behavior and the permeability (SFC) are, for example, inorganic inert substances, organic polymers, cationic polymers and di- or polyvalent metal cations. Suitable coatings for dust binding are, for example, polyols.

Suitable inorganic inert substances are silicates such as montmorillonite, kaolinite and talc, zeolites, activated carbons, polysilicic acids, magnesium carbonate, calcium carbonate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as a dispersion in an aqueous or water-miscible dispersant or in substance.

When the water-absorbing polymer particles are coated with an inorganic inert material, the amount of inorganic inert material used, based on the water-absorbing polymer particles, is preferably from 0.05 to 5% by weight, more preferably from 0.1 to 1.5% by weight, most preferably from 0.3 to 1% by weight.

Suitable organic materials are polyalkyl methacrylates or thermoplastics such as polyvinyl chloride.

Suitable cationic polymers are polyalkylenepolyamines, cationic derivatives of polyacrylamides, polyethyleneimines and polyquaternary amines.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or polyfunctional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine.

The cationic polymers may be used as a solution in an aqueous or water-miscible solvent, as a dispersion in an aqueous or water-miscible dispersant or in substance.

When the water-absorbing polymer particles are coated with a cationic polymer, the use amount of cationic polymer based on the water-absorbing polymer particles is preferably from 0.1 to 15% by weight, more preferably from 0.5 to 10% by weight, most preferably from 1 to 5% by weight.

When a continuous horizontal mixer is used for the coating with a cationic polymer, the residence time of the water-absorbing polymer particles before the cationic polymer is sprayed on is preferably from 2 to 50% by weight, more preferably from 5 to 30% by weight, most preferably from 10 to 25% by weight, of the total residence time in the mixer.

Suitable di- or polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, nitrate and sulfate. The metal salts are preferably used as a solution. The solvents used for the metal salts may be water, alcohols, dimethylformamide, dimethyl sulfoxide and mixtures thereof. Particular preference is given to water and water/alcohol mixtures, such as water/methanol or water/propylene glycol.

The liquid sprayed in the process according to the invention preferably comprises at least one polyvalent metal cation, for example $Al^{3+}$.

When the water-absorbing polymer particles are coated with a polyvalent metal cation, the amount of polyvalent metal cation used, based on the water-absorbing polymer particles, is preferably from 0.05 to 5% by weight, more preferably from 0.1 to 1.5% by weight, most preferably from 0.3 to 1% by weight.

When a continuous horizontal mixer is used for the coating with a cationic polymer and a polyvalent metal cation, the residence time of the water-absorbing polymer particles before the polyvalent metal cation is sprayed on is preferably from 1 to 30%, more preferably from 2 to 20%, most preferably from 5 to 15%, of the total residence time in the mixer. Advantageously, the polyvalent metal cation is metered in before the cationic polymer.

Particularly suitable polyols are polyethylene glycols having a molecular weight of from 400 to 20 000 g/mol, polyglycerol, 3- to 100-tuply ethoxylated polyols, such as trimethylolpropane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbing polymer particles only insignificantly. The polyols are preferably used as a solution in aqueous or water-miscible solvents.

The liquid sprayed in the process according to the invention preferably comprises at least one polyol, for example polyethylene glycol.

When the water-absorbing polymer particles are coated with a polyol, the use amount of polyol, based on the water-absorbing polymer particles, is preferably from 0.005 to 2% by weight, more preferably from 0.01 to 1% by weight, most preferably from 0.05 to 0.5% by weight.

When a continuous horizontal mixer is used for the coating with a cationic polymer and a polyol, the residence time of the water-absorbing polymer particles before the polyol is sprayed on is preferably from 20 to 80%, more preferably from 30 to 70%, most preferably from 40 to 60%, of the total residence time in the mixer. Advantageously, the polyol is metered in after the cationic polymer.

The abovementioned coatings can, though, also be applied to polymer particles (base polymer) which have not been postcrosslinked.

The process according to the invention is suitable both for spraying the postcrosslinker solution and for spraying other abovementioned liquids on to water-absorbing polymer particles.

The process according to the invention enables uniform coating of the water-absorbing polymer particles and hence the production of polymer particles with high permeability (SFC) and low dust content.

Moreover, only a low level of agglomerates form in the process according to the invention. In addition, the process is not prone to disruption owing to the reduced blocking tendency of the spray nozzles to be used in accordance with the invention.

The process according to the invention is also suitable for coating with thermally sensitive substances.

The water-absorbing polymer particles obtainable by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g.

The water-absorbing polymer particles obtainable by the process according to the invention have an absorbency under a load of 6.21 kPa (AUL0.9 psi) of typically at least 10 g/g, preferably at least 12 g/g, preferentially at least 14 g/g, more preferably at least 16 g/g, most preferably at least 18 g/g, and typically not more than 30 g/g.

The water-absorbing polymer particles obtainable by the process according to the invention have a saline flow conductivity (SFC) of typically at least $100 \times 10^{-7}$ cm$^3$s/g, usually at least $200 \times 10^{-7}$ cm$^3$s/g, preferably at least $300 \times 10^{-7}$ cm$^3$s/g, preferentially at least $350 \times 10^{-7}$ cm$^3$s/g, more preferably at least $400 \times 10^{-7}$ cm$^3$s/g, most preferably at least $450 \times 10^{-7}$ cm$^3$s/g, and typically not more than $700 \times 10^{-7}$ cm$^3$s/g.

The water-absorbing polymer particles are tested by the test methods described below.

Methods:

The measurements should, unless stated otherwise, be performed at an ambient temperature of 23±2° C. and a relative air humidity of 50±10%. The water-absorbing polymer particles are mixed thoroughly before the measurement.

Particle Size Distribution (PSD)

The particle size distribution of the water-absorbing polymer particles is determined analogously to the EDANA (European Disposables and Nonwovens Association) recommended test method No. WSP 220.2-05 "Particle size distribution".

Centrifuge Retention Capacity (CRC)

The centrifuge retention capacity is determined analogously to the EDANA (European Disposables and Nonwovens Association) recommended test method No. WSP 241.2-05 "Centrifuge retention capacity", the water-absorbing polymer particles being screened before the measurement to the particle size range from greater than 300 to 600 µm.

Absorbency Under Load (AUL0.9 psi)

The absorbency under a load of 6.21 kPa (0.9 psi) of the water-absorbing polymer particles is determined analogously to the EDANA (European Disposables and Nonwovens Association) recommended test method No. WSP 242.2-05 "Absorption under pressure", using 0.16 g of water-absorbing polymer particles with a particle size range of from greater than 300 to 600 µm instead of 0.9 g of water-absorbing polymer particles, using a wire mesh with a mesh width of 149 µm instead of a mesh width of 36 µm as the base plate and using a weight of 63 g/cm$^2$ (0.9 psi) instead of a weight of 21 g/cm$^2$ (0.3 psi).

Extractables 16 h

The content of extractable constituents in the water-absorbing polymer particles is determined by the EDANA (European Disposables and Nonwovens Association) recommended test method No. WSP 270.2-05 "Extractables".

Saline Flow Conductivity (SFC)

The saline flow conductivity of a swollen gel layer under a pressure of 21 g/cm$^2$ (0.3 psi) is, as described in EP 0 640 330 A1, determined as the gel layer permeability of a swollen gel layer of water-absorbing polymer particles, except that the apparatus described in the aforementioned patent application on page 19 and in FIG. 8 has been modified to the effect that the glass frit (40) is not used, the die (39) consists of the same polymer material as the cylinder (37) and now comprises 21 bores of equal size distributed uniformly over the entire contact surface. The procedure and evaluation of the measurement remain unchanged from EP 0 640 330 A1. The flow rate is recorded automatically.

The saline flow conductivity (SFC) is calculated as follows:

$$SFC\ [\text{cm}^3\text{s/g}] = (Fg(t=0) \times L0)/(d \times A \times WP),$$

where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in g/cm$^3$, A is the area of the gel layer in cm$^2$ and WP is the hydrostatic pressure over the gel layer in dyn/cm$^2$.

Dust Count

The dust count of the water-absorbing polymer particles is determined with the aid of the DustView dust measurement unit (Palas GmbH, Karlsruhe, Germany).

The mechanical part of the measuring instrument consists of a charging funnel with flap, downpipe and dust casing with removable dust box.

The determination of the dust count quantitatively records dusting fractions of solids which arise after defined stress on the material (free fall and collision).

The evaluation is effected by optoelectronic means. The dusting solids content leads to the attenuation of a light beam, which is recorded photometrically. The measurement registration and evaluation are effected in the control unit. The following measurements are indicated as numerical values on the control unit:

1. measurement after 0.5 second (maximum value)
2. measurement after 30 seconds (dust value)
3. dust count (sum of maximum value and dust value)

The dust counts are rated as follows:
dust count 25-100 dusting to highly dusting
dust count 12-25 low-dusting to dusting
dust count 1-12 low-dusting to virtually dust-free
dust count ≤1 dust-free The EDANA test methods are obtainable, for example, from European Disposables and Nonwovens Association, Avenue Eugene Plasky 157, B-1030 Brussels, Belgium.

EXAMPLES

The examples were performed with commercial water-absorbing polymer particles based on sodium acrylate.

Such water-absorbing polymer particles are commercially available, for example, from BASF Aktiengesellschaft (trade name HySorb®), from Stockhausen GmbH (trade name Favor®) and from Nippon Shokubai Co., Ltd. (trade name Aqualic®).

The water-absorbing polymer particles used had the following property profile:

| | |
|---|---|
| CRC: | 26.5 g/g |
| AUL0.9 psi: | 21 g/g |
| SFC: | $120 \times 10^{-7}$ cm$^3$s/g |
| Extractables 16 h: | 7.8% by weight |
| PSD: >850 µm | 0.7% by weight |
| 600-850 µm | 31.3% by weight |
| 300-600 µm | 50.5% by weight |
| 90-300 µm | 17.3% by weight |
| <90 µm | 0.2% by weight |

Example 1

The water-absorbing polymer particles were coated in a Ruberg DLM 350-1500 continuous flow mixer (Gebrüder Ruberg GmbH & Co KG, Nieheim, Germany) by means of an RZD1-H two-substance nozzle (Gebrüder Ruberg GmbH & Co KG, Nieheim, Germany) with a 50% by weight aqueous solution of Lupamin® 9095 (BASF Aktiengesellschaft, Ludwigshafen, Germany). Lupamin® 9095 is a high molecular weight linear polyvinylamine.

The continuous flow mixer had a mixing chamber volume of 140 l. The fill level of the continuous flow mixer was 60% and the speed was 43 min$^{-1}$. The Froude number of the moving water-absorbing polymer particles was 0.36.

The two-substance nozzle was installed horizontally. The distance from the end wall of the continuous flow mixer was 375 mm and the horizontal distance of the nozzle mouth from the mixer wall was 50 mm. The nozzle head was immersed completely into the water-absorbing polymer particles. The spray nozzle had electrical trace heating. The trace heating was regulated such that the nozzle temperature was from 65 to 70° C.

The throughput of water-absorbing polymer particles was 180 kg/h. The temperature of the water-absorbing polymer particles was 60° C.

The throughput of coating solution was 7.2 kg/h. The temperature of the coating solution was 60° C.

The continuous flow mixer was operated without disruption for several hours.

The coated water-absorbing polymer particles were analyzed. The results are compiled in Table 1.

Example 2 (Comparative Example)

The procedure of Example 1 was repeated, except that the two-substance nozzle was not heated.

The continuous flow mixer was operated without disruption for several hours.

The coated water-absorbing polymer particles were analyzed. The results are compiled in Table 1.

TABLE 1

Coating with Lupamin ® 9095

| Example | CRC | AUL0.9 psi | SFC | PSD >850 µm |
|---|---|---|---|---|
| 1 | 27 g/g | 19 g/g | $381 \times 10^{-7}$ cm$^3$/s/g | 0.8% by wt. |
| 2*) | 26 g/g | 18 g/g | $257 \times 10^{-7}$ cm$^3$/s/g | 12% by wt. |

*)comparative example

Example 3

The procedure of Example 1 was repeated. In addition, coating with a 20% by weight aqueous solution of polyethylene glycol-400 (polyethylene glycol having a mean molar mass of 400 g/mol) was effected by means of a second two-substance nozzle.

The second two-substance nozzle was likewise installed horizontally. The distance from the end wall of the continuous flow mixer was 750 mm and the horizontal distance of the nozzle mouth from the mixer wall was 50 mm. The nozzle head was immersed completely into the water-absorbing polymer particles.

The throughput of coating solution was 1.35 kg/h. The temperature of the coating solution was 20° C.

The continuous flow mixer was operated without disruption for several hours.

The coated water-absorbing polymer particles were analyzed. The results are compiled in Table 2.

Example 4 (Comparative Example)

The procedure of Example 3 was repeated, except that the two-substance nozzle was not heated.

The continuous flow mixer was operated without disruption for several hours.

The coated water-absorbing polymer particles were analyzed. The results are compiled in Table 2.

TABLE 2

Coating with Lupamin ® 9095 and polyethylene glycol-400

| Example | CRC | AUL0.9 psi | SFC | Dust count |
|---|---|---|---|---|
| 3 | 26 g/g | 21 g/g | $190 \times 10^{-7}$ cm$^3$s/g | —**) |
| 4*) | 26 g/g | 21 g/g | $170 \times 10^{-7}$ cm$^3$s/g | 0.7 |

*)comparative example
**)below the lower detection limit

Example 5

The procedure of Example 3 was repeated. In addition, coating with a 23.9% by weight aqueous solution of aluminum sulfate was effected by means of a third two-substance nozzle.

The third two-substance nozzle was likewise installed horizontally. The distance from the end wall of the continuous flow mixer was 150 mm and the horizontal distance of the nozzle mouth from the mixer wall was 50 mm. The nozzle head was immersed completely into the water-absorbing polymer particles.

The throughput of coating solution was 7.2 kg/h. The temperature of the coating solution was 20° C.

The continuous flow mixer was operated without disruption for several hours.

The coated water-absorbing polymer particles were analyzed. The results are compiled in Table 3.

Example 6 (Comparative Example)

The procedure of Example 5 was repeated, except that the two-substance nozzle was not heated.

The continuous flow mixer was operated without disruption for several hours.

The coated water-absorbing polymer particles were analyzed. The results are compiled in Table 3.

TABLE 3

| | Coating with Lupamin® 9095, polyethylene glycol-400 and aluminum sulfate | | |
|---|---|---|---|
| Example | CRC | AUL0.9 psi | SFC |
| 5 | 23 g/g | 17 g/g | 456 × 10$^{-7}$ cm$^3$s/g |
| 6*) | 24 g/g | 17 g/g | 413 × 10$^{-7}$ cm$^3$s/g |

*)comparative example

Example 7

The water-absorbing polymer particles were coated in a 5 MK Pflugschar® plowshare mixer (Gebrüder Lödige Maschinenbau GmbH, Paderborn, Germany) with a 50% by weight aqueous solution of Lupamin® 9095 (BASF Aktiengesellschaft, Ludwigshafen, Germany) by means of a 970 S4 two-substance nozzle having a diameter of 0.8 mm (Düsen-Schlick GmbH, Untersiemau, Germany). Lupamin® 9095 is a high molecular weight linear polyvinylamine.

The Pflugschar® mixer was initially charged with 1890 g of water-absorbing polymer particles. The temperature of the water-absorbing polymer particles was 60° C. The fill level of the Pflugschar® mixer was 60% and the speed was 90 min$^{-1}$.

The two-substance nozzle was installed vertically. The distance from the water-absorbing polymer particles was 100 mm. The spray nozzle was preheated to 65° C. and insulated. The initial pressure of the atomizer gas was 3 bar. The throughput of atomizer gas was 2 kg/h.

Within 4 minutes, 76 g of coating solution were sprayed on and the mixture was stirred for a further 11 minutes. The initial pressure of the coating solution was 0.3 bar. The temperature of the coating solution was 65° C.

The Pflugschar® mixer was operated without disruption.

The coated water-absorbing polymer particles were analyzed. The coated water-absorbing polymer particles had a centrifuge retention capacity (CRC) of 26 g/g, an absorbency under load (AUL0.9 psi) of 19 g/g, a saline flow conductivity (SFC) of 395×10$^{-7}$ cm$^3$s/g and 0.9% by weight of particles larger than 850 μm.

Example 8 (Comparative Example)

The procedure of Example 7 was repeated, except that the two-substance nozzle was not insulated.

Deposits at the nozzle mouth led to deflection and narrowing of the spray cone up to and including blockage. The water-absorbing polymer particles were coated inhomogeneously. Many lumps formed.

The invention claimed is:

1. A process for producing water-absorbing polymer particles by polymerizing a monomer solution or suspension comprising
    a) at least one ethylenically unsaturated acid-bearing monomer which may be at least partly neutralized,
    b) at least one crosslinker,
    c) optionally one or more ethylenically and/or allylically unsaturated monomers copolymerizable with the monomers specified under a), and
    d) optionally one or more water-soluble polymers,
    followed by drying, grinding, classifying, and optionally postcrosslinking the polymerized material into water-absorbing polymer particles, and then spraying a liquid onto the water-absorbing polymer particles using at least one spray nozzle in a horizontal mixer, wherein the at least one spray nozzle is thermally insulated and/or trace-heated,
    a temperature of the at least one spray nozzle is from 1 to 20° C. higher than a temperature of the water-absorbing polymer particles, and
    the water-absorbing polymer particles are moved in the horizontal mixer with a speed which corresponds to a Froude number of from 0.1 to 0.7.

2. The process according to claim 1, which comprises at least one postcrosslinking.

3. The process according to claim 2, wherein the liquid is sprayed onto postcrosslinked polymer particles.

4. The process according to claim 1, wherein a continuous mixer is used.

5. The process according to claim 1, wherein a fill level of the mixer is from 30 to 80%.

6. The process according to claim 1, wherein the water-absorbing polymer particles fed to the mixer have a water content of less than 20% by weight.

7. The process according to claim 1, wherein the water-absorbing polymer particles fed to the mixer have a temperature of from 40 to 80° C.

8. The process according to claim 1, wherein a thermally insulated spray nozzle is used and a temperature of the liquid to be sprayed is from 1 to 20° C. higher than a temperature of the water-absorbing polymer particles.

9. The process according to claim 1, wherein a trace-heated and optionally thermally insulated spray nozzle is used and a temperature difference between the water-absorbing polymer particles and the liquid to be sprayed is less than 20° C.

10. The process according to claim 1, wherein the liquid is sprayed using a two-substance nozzle.

11. The process according to claim 10, wherein a temperature difference between the liquid to be sprayed and an atomizer gas is less than 20° C.

12. The process according to claim 1, wherein a residence time of the water-absorbing polymer particles in the horizontal mixer is from 1 to 180 minutes.

13. The process according to claim 1, wherein a peripheral speed of mixing tools in the horizontal mixer is from 0.1 to 10 m/s.

14. The process according to claim 1, wherein the liquid is an aqueous solution or dispersion.

15. The process according to claim 1, wherein the liquid comprises at least one polyamine.

16. The process according to claim 1, wherein the liquid comprises at least one polyol.

17. The process according to claim 1, wherein the liquid comprises at least one polyvalent metal cation.

18. The process according to claim 1, wherein the water-absorbing polymer particles have a centrifuge retention capacity of at least 15 g/g.

19. The process according to claim 1, wherein the temperature of the at least one spray nozzle is from 2 to 15° C. higher than a temperature of the water-absorbing polymer particles.

20. The process according to claim 1, wherein the temperature of the at least one spray nozzle is from 5 to 10° C. higher than a temperature of the water-absorbing polymer particles.

* * * * *